United States Patent [19]

Hayashi et al.

[11] Patent Number: 5,792,662
[45] Date of Patent: Aug. 11, 1998

[54] METHOD OF DETERMINATION OF FLUORESCENT SUBSTANCE AND METHOD OF ASSAY OF ENZYME ACTIVITY

[75] Inventors: Hidechika Hayashi, Kanagawa; Kazuya Kamata, Toyama, both of Japan

[73] Assignee: Tosoh Corporation, Shinnanyo, Japan

[21] Appl. No.: 842,405

[22] Filed: Apr. 24, 1997

Related U.S. Application Data

[63] Continuation of Ser. No. 551,490, Nov. 1, 1995, abandoned.

[30] Foreign Application Priority Data

Nov. 8, 1994 [JP] Japan ................................ 6-273746

[51] Int. Cl.$^6$ ................................................ G01N 21/64
[52] U.S. Cl. ...................... 436/8; 436/172; 435/4; 250/459.1
[58] Field of Search ................. 436/8, 172; 250/459.1; 435/7.4, 7.9, 968, 4

[56] References Cited

U.S. PATENT DOCUMENTS

| | | | |
|---|---|---|---|
| 4,788,138 | 11/1988 | Tung et al. | 435/7 |
| 4,990,784 | 2/1991 | Dukes et al. | 250/358.1 |
| 5,460,943 | 10/1995 | Hayashi et al. | 435/7.4 |

FOREIGN PATENT DOCUMENTS

| | | |
|---|---|---|
| 0 278 149 A2 | 8/1988 | European Pat. Off. . |
| 0521636 | 1/1993 | European Pat. Off. . |
| WO 92/13264 | 8/1982 | WIPO . |

OTHER PUBLICATIONS

Mickley, H.S. et al. "Applied Mathematics in Chemical Engineering" Second Edition, McGraw Hill Book Company, New York, pp. 8–15 (1957).

*Primary Examiner*—Jeffrey Snay
*Attorney, Agent, or Firm*—Oblon, Spivak, McClelland, Maier & Neustadt, P.C.

[57] ABSTRACT

A method for determining a fluorescent substance in a broader concentration range with higher measurement accuracy is provided which is applicable to assay of enzyme activity in enzyme-label immunoassay, enzyme-label DNA hybridization, etc. A method for assaying enzyme activity is also provided which employs the above fluorescence measurement. In the method, a specimen containing an objective fluorescent substance to be determined and a reference substance is irradiated with excitation light capable of exciting both the objective fluorescent substance and the reference fluorescent substance; measuring a first fluorescence intensity at a first wavelength where fluorescence is emitted mainly by the objective fluorescent substance; measuring a second fluorescence intensity at a second wavelength where fluorescence is emitted mainly by the reference fluorescent substance; and calculating the concentration of the objective fluorescent substance from the equation:

$$1/(y-c) = a/x + b$$

where x is the concentration of the objective fluorescent substance, and y is a ratio of the first fluorescence intensity to the second fluorescence intensity.

5 Claims, 7 Drawing Sheets

EXCITATION WAVELENGTH

FIG. 2B

FLUORESCENCE WAVELENGTH

FIG. 7  4-METHYLUMBELLIFERONE CONCENTRATION nM

METHOD OF DETERMINATION OF FLUORESCENT SUBSTANCE AND METHOD OF ASSAY OF ENZYME ACTIVITY

This application is a Continuation of application Ser. No. 08/551,490, filed on Nov. 1, 1995, now abandoned.

BACKGROUND OF THE INVENTION

1. Field of the Invention

The present invention relates to a method of determination of a fluorescent substance, and to a method of assay of an enzyme activity.

2. Description of the Related Art

Conventionally, immuunoassay using an enzyme or a fluorescent substance as a label, or enzyme- or fluorescent substance-label DNA hybridization is employed for detection or determination of a micro quantity of a biological substance. For such purposes, the enzyme activity measurement methods are widely employed in which the concentration of a fluorescent substance is allowed to change by action of the enzyme during the measurement, because the methods make practicable the measurement of enzyme activity in high sensitivity in a short time in comparison with light absorption methods or other enzyme activity measurement.

In recent years, as the determination of a micro quantity of a substance becomes important in clinical diagnosis, measurement of finer amounts of biological materials with higher sensitivity has come to be required. Further, since the concentrations of trace components in a specimen distribute in a broad range, a measuring method is demanded which is capable of measuring a high concentration of an objective substance without dilution, namely a wide-range measurement method.

For fluorometric measurement, the hardware, namely the measurement apparatus, is being improved so as to conduct rapid fluorescence measurement of a large number of samples, or to conduct fluorescence measurement without contamination between the samples. For example, fluorescence is measured with an optical system called a top-top optical system in which excitation light is projected from the top of the sample downward, and the fluorescence emitted upward is measured at the top, thereby a large number of fluorescence intensities can be measured without contamination between the specimens.

On the other hand, the software is also being improved to measure the fluorescence intensity with high sensitivity and high precision. For example, the inventors of the present invention disclosed, in Japanese Patent Laid-Open Publication 5-38297, a method for assaying an enzyme activity, which comprises steps of irradiating excitation light to a specimen containing an enzyme and a substance (substrate) changeable by action of the enzyme, measuring the intensity of fluorescence emitted from the specimen at a prescribed wavelength selectively, and deriving the enzyme activity from the measured fluorescence intensity, wherein another substance (a fluorescent reference substance) which is not susceptible to the enzyme is added to the specimen; a first fluorescence intensity is measured at a first wavelength where most of the fluorescence comes from the objective fluorescent substance, and a second fluorescence intensity is measured at a second wavelength where the fluorescence comes from the fluorescent reference substance; and the enzyme activity is derived from the quotient (or ratio) obtained by dividing the first fluorescence intensity by the second fluorescence intensity.

Such a method makes possible the correction of the drop of the apparent value of the measured fluorescence intensity caused by self-absorption of excitation light at a high concentration of the objective fluorescent substance.

However, the aforementioned method of utilizing the ratio of the fluorescence intensity of the objective fluorescent substance to that of the reference fluorescent substance was found to involve a problem such that, at an extremely high concentration of the objective fluorescent substance, the second fluorescence light intensity includes the reference fluorescence light intensity and a fraction of the fluorescence light intensity of the objective substance, thereby causing deviation of the measured value from the inherent linear relation between the objective substance concentration and the measured fluorescence intensity ratio. Generally, the fluorescence spectrum of a substance has a broad wavelength distribution, it is difficult to separate completely the fluorescence of the objective fluorescent substance from that of the reference fluorescent substance. Accordingly, the aforementioned method has still to be improved although the measurement range is broad advantageously in comparison with the prior art techniques. The present invention has been made to solve the above problems.

SUMMARY OF THE INVENTION

The present invention intends to provide a method for determining a fluorescent substance in a broader concentration range with higher accuracy, the method being applicable to assay of enzyme activity in enzyme-label immunoassay, enzyme-label DNA hybridization.

The present invention also intends to provide a method for assaying enzyme activity employing the above fluorescence measurement.

The method for determining a fluorescent substance of the present invention comprises adding a known amount of a fluorescent substance (reference fluorescent substance) as a reference to a specimen containing an objective fluorescent substance to be determined; irradiating the specimen with excitation light capable of exciting both the objective fluorescent substance and the reference fluorescent substance; measuring a first fluorescence intensity at a first wavelength where fluorescence is emitted mainly by the objective fluorescent substance; measuring a second fluorescence intensity at a second wavelength where fluorescence is emitted mainly by the reference fluorescent substance; and deriving the concentration of the objective fluorescent substance from the equation:

$$1/(y-c) = a/x + b$$

where x is the concentration of the objective fluorescent substance, y is a ratio of the first fluorescence intensity to the second fluorescence intensity, and a, b, and c are parameters derived experimentally.

The method for assaying activity of an enzyme of the present invention measures change with time of concentration of an objective fluorescent substance by the action of the enzyme, and comprises adding a known amount of a fluorescent substance (reference fluorescent substance) as a reference to a specimen containing an objective fluorescent substance to be determined; irradiating the specimen with excitation light capable of exciting both the objective fluorescent substance and the reference fluorescent substance; measuring a first fluorescence intensity at a first wavelength where fluorescence is emitted mainly by the objective fluorescent substance; measuring a second fluorescence intensity at a second wavelength where fluorescence is emitted mainly by the reference fluorescent substance; deriving the concentration of the objective fluorescent substance from the equation:

$$1/(y-c)=a/x+b$$

where x is the concentration of the objective fluorescent substance, and y is a ratio of the first fluorescence intensity to the second fluorescence intensity; and deriving the activity of the enzyme or the concentration of the enzyme from the change with time of the value of x.

BRIEF DESCRIPTION OF THE DRAWINGS

In FIGS. 1A and 1B, the ordinate axes show the fluorescence intensity, and the abscissa axes show wavelength (nm).

In FIGS. 2A and 2B, the ordinate axes show the fluorescence intensity, and the abscissa axes show wavelength (nm).

$$1/(y+0.01)=(1.048\times10^3)/x+0.0193$$

the calibration curve (b) is represented by the quadratic equation:

$$y=(-9\times59\times10^{-9})x^2+(0.901\times10^{-3})x-0.01$$

and the calibration curve (c) is represented by the linear equation:

$$y=(0.805\times10^3)x-0.01$$

In FIG. 6, the solid rhombus symbols (☆) show the data calculated by linear conversion, the solid square symbols (■) show the data calculated by the quadratic equation, and the solid triangle symbols (▲) show the data calculated according to the present invention.

$$1/(y+0.01)=(1.048\times10^3)/x+0.0192$$

the calibration curve (b) is represented by the quadratic equation:

$$y=(-5.46\times10^{-9})x^2+(0.767\times10^{-3})x+0.43$$

DETAILED DESCRIPTION OF THE PREFERRED EMBODIMENT

The present invention is achieved on the basis of the findings of the relation of an apparent fluorescence intensity decreased by various causes to the real value, in particular, at high concentrations of an objective fluorescent substance. The method is characterized by determination of the concentration of an objective fluorescent substance which changes its concentration by action of an enzyme according to the equation: $1/(y-c)=a/x+b$. Naturally, in enzyme immunoassay, etc., the measured concentration of the objective fluorescent substance depends on the concentration of labeling enzyme. The enzyme may be in a free state in a solution such as a reaction solution, or may be immobilized to a solid phase by an antigen or an antibody in immunoassay.

In enzyme activity measurement by fluorometry, a substrate is usually used which is converted by action of an enzyme into a fluorescent enzymatic reaction product, but in some cases a fluorescent substrate is used which is converted by action of an enzyme into a non-fluorescent enzymatic reaction product. In any case, the measurement utilizes change of the objective fluorescent substance.

In the case where the concentration of the objective fluorescent substance changes with time and the intensity of the fluorescence changes correspondingly, for example, in the aforementioned enzymatic immunoassay according to the present invention, the concentration of the objective fluorescent substance is quantitatively determined first and then the rate of the change concentration of the objective fluorescent substance with time (increase or decrease, so-called "Rate" value) is calculated; and the enzyme concentration is determined by reference to a calibration curve having been prepared for the relation between the concentration of the enzyme and the rate (the change of the concentration of the objective fluorescent substance with time). When a substrate is converted enzymatically into a fluorescent reaction product, the Rate is a positive value and is positively correlative to the enzyme concentration, and when a fluorescent substrate is converted enzymatically into a non-fluorescent reaction product, the Rate is negative. Specifically, the concentration of the fluorescent substance is derived from the value of "y" which is a ratio of the first fluorescence intensity to the second fluorescence intensity according to the equation: $1/(y-c)=a/x+b$, and the Rate is derived from the time while the enzyme reacts and the change of the concentration of the fluorescent substance during the time. The rate is constant under the adequate reaction condition so the concentration of the enzyme, that is, the activity of enzyme can be calculated from more than two concentration of an objective fluorescent substance is one of the reference specimens is zero. It is required to improve the accuracy of conversion in a low concentration of the objective fluorescent substance that the concentration of an objective fluorescent substance in one of the reference specimens is nearly zero.

The reference fluorescent substance is selected from substances having an excitation spectrum overlapping with that of the objective fluorescent substance but having an emission spectrum overlapping as little as possible with that of the objective fluorescent substance. Therefore, the reference fluorescent substance should be selected in consideration of the fluorescence characteristics of the objective substance. The concentration of the enzyme is usually measured by the enzymatic activity which is assayed under the definite condition. For example, in this paper, the concentration of alkaline Phosphatase is measured by the enzymatic activity which decomposes 4-methylumbelliferyl phosphate under 0.5M Aminomethylpropenol buffer(pH10).

The wavelength of the excitation light is selected from the wavelength range in which both of the objective fluorescent substance and the reference fluorescent substance can be simultaneously excited. The wavelength for measurement of the first fluorescence intensity (first measurement wavelength) is selected from the wavelength range of the fluorescence light emitted from the objective fluorescent substance by irradiation of the excitation light, and the wavelength for measurement of the second fluorescence intensity (second measurement wavelength) is selected from the wavelength range of the fluorescence light emitted from the reference fluorescent substance by irradiation of the same excitation light.

The concentration of the reference fluorescent substance is selected such that the self-absorption of the excitation light is low and the fluorescence intensity at the second measurement wavelength is sufficiently high. When the emission spectrum of the objective fluorescent substance overlaps with the spectrum of the excitation light of the reference fluorescent substance, the fluorescence is re-absorbed by the reference fluorescent substance. Therefore, the concentration of the reference fluorescent substance is selected such that the above absorption of the fluorescence is not excessively high. In the case where the reference fluorescent substance absorbs significantly the fluorescence at the first measurement wavelength (re-absorption), the concentration of the reference fluorescent substance is decided usually such that the absorption is not more than 20%, preferably not more than 10% of the total fluorescence of the objective fluorescent substance.

For measurement of the fluorescence, the specimen is usually placed in a small container or a cuvette. The enzyme, which activity generates the objective fluorescent substance, includes free natural enzyme, enzymes bonded to an antigen, an antibody, DNA, etc., and enzymes bonded indirectly to a surface of a solid in enzyme-label immunoassay, enzyme-label DNA hybridization, etc. Therefore, the specimen for the fluorescence measurement includes not only solutions of a fluorescent substance but also enzyme-containing solutions, and a liquid containing a solid phase left by B/F separation (bind/free separation) in enzymatic immune reaction, etc.

In enzyme-label immunoassay and enzyme-label DNA hybridization, alkaline phosphatase, β-galactosidase, or the like is employed as the labeling enzyme. The substrate which changes fluorescence intensity by action of the alkaline phosphatase is exemplified by 4-methylumbelliferyl phosphate, etc. The 4-methylumbelliferyl phosphate is converted to 4-methylumbelliferone by action of the enzyme. The substrate which changes its fluorescence intensity by action of the β-galactosidase is exemplified by 4-methylumbelliferyl galactoside, etc. This 4-methylumbelliferyl galactoside is converted to 4-methylumbelliferone by action of the enzyme.

Figure 1A:
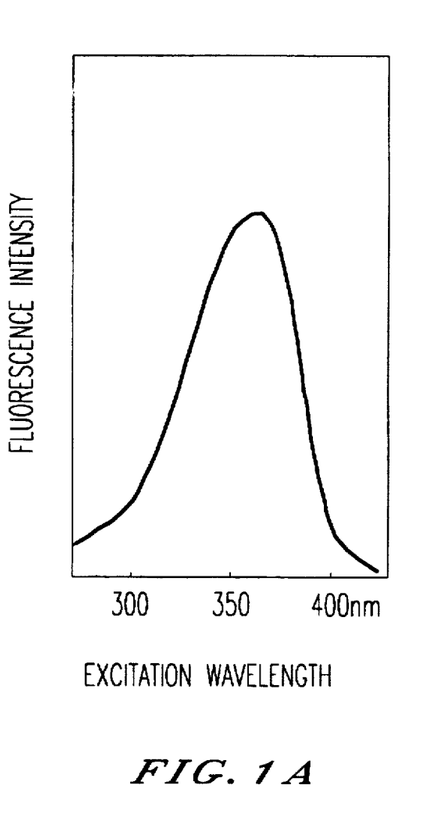
FIG. 1A shows an excitation spectrum, at pH 10, of 4-methylumbelliferone (20 µM), which is a product of the enzymatic reaction of 4-methylumbelliferyl phosphate with alkaline phosphatase, for causing fluorescence at 450 nm.
Figure 1B:
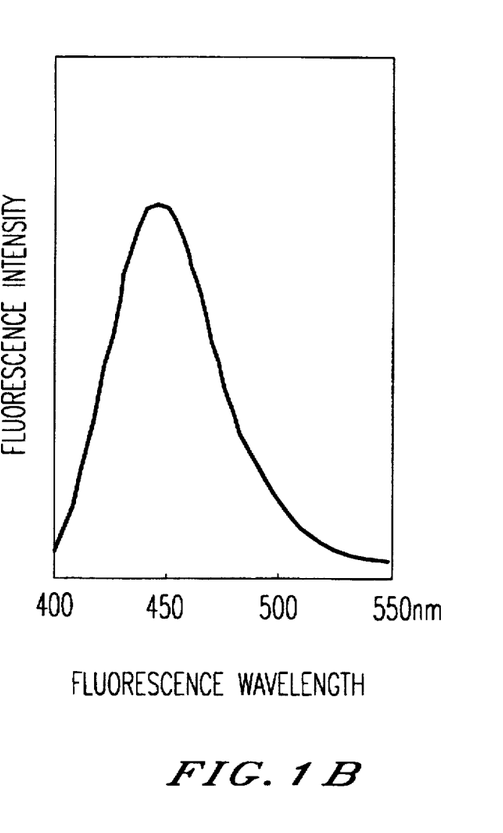
FIG. 1B shows an emission spectrum thereof for the excitation light of 365 nm.

FIG. 1A shows an excitation spectrum of 4-methylumbelliferone at pH 10, and FIG. 1B shows an emission spectrum thereof at the same pH. On irradiation of excitation light having wavelength at 365 nm, 4-methylumbelliferone emits fluorescence having the maximum at 450 nm, but 4-methylumbelliferyl phosphate and 4-methylumbelliferyl galactoside do not emit the fluorescence in the same wavelength region. Therefore, in practicing the present invention employing 4-methylumbelliferone as the objective fluorescent substance, the enzyme activity is measured preferably with excitation light of 365 nm, and the first measurement wavelength of about 450 nm. The reference fluorescent substance therefor is preferably selected which emits, by excitation light of 365 nm, fluorescence differentiable from the fluorescence maximum of about 450 nm of 4-methylumbelliferone, e.g., fluorescence at 500 nm or a longer wavelength. Examples of the reference fluorescent substance having such fluorescence characteristics are shown below:

| (Chemical structure) | $(E_x^{max})$ (nm) | $(E_m^{max})$ (nm) |
|---|---|---|
| (1) Dansyl compounds: | | |
| Dansylsulfonic acid | 325 | 550 |

| (Chemical structure) | $(E_x^{max})$ (nm) | $(E_m^{max})$ (nm) |
|---|---|---|
| Dansyl chloride | 325 | 550 |
| Dansyl amino acid (Example) Dansyl-L-alanine | 325 | 550 |
| Dansyl hydrazine | 340 | 525 |
| (2) 4-Dimethylamino-1-naphthoylnitrile | 350 | 530 |
| (3) N-(1-anilinonaphthyl)-4-maleimide | 350 | 530 |
| (4) 7-Benzylamino-4-nitrobenzo-2-oxa-1,3-diazole (R = H), and 7-(p-Methoxybenzylamino)-4-nitrobenz-2-oxa-1,3-diazole (R = OCH₃) | 340 | 530 or 458 |

Although the maximums of the excitation spectra of the above reference fluorescent substances are different from 365 nm, the reference substance emits fluorescence on irradiation of excitation light of 365 nm since the excitation spectrum of the substance extends to 365 nm. As the spectrums of 4-methylumbelliferone overlaps slightly with that of the above reference fluorescent substance, the measured fluorescence at the first measurement wavelength of 450 nm may include some fluorescence emitted by the reference fluorescent substance. However, the intensity of the fluorescence light of the reference fluorescent substance contaminated by the first measurement wavelength light is nearly constant and slight. Therefore the contamination of the fluorescence affects little the ratio (y) of the measured fluorescence intensity at the first measurement wavelength to that at the second measurement wavelength, and the rate of the change of the ratio with time.

On the other hand, the fluorescence measured at the second measurement wavelength may include a portion of the fluorescence of 4-methylumbelliferone. At a higher concentration of 4-methylumbelliferone, the intermixing portion of the fluorescence of 4-methylumbelliferone at the second measurement wavelength will be larger. Thereby the ratio of the first fluorescence intensity to the second fluorescence intensity is not proportional to the concentration of the objective fluorescent substance, because not only the numerator is proportional to its concentration but also the denominator depends on its concentration at a high concentration. Therefore, it is particularly desired to select the measurement wavelength to avoid the unwanted mixing of the fluorescence of the objective fluorescent substance to the fluorescence at the second measurement wavelength.

Figure 2A:
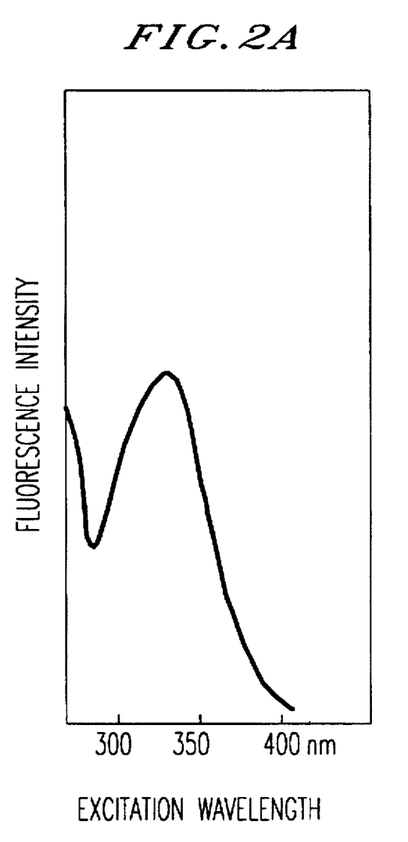
FIG. 2A shows an excitation spectrum of dansylalanine (10 µg/mL) which is a reference fluorescent substance emitting the fluorescence at 550 nm.
Figure 2B:
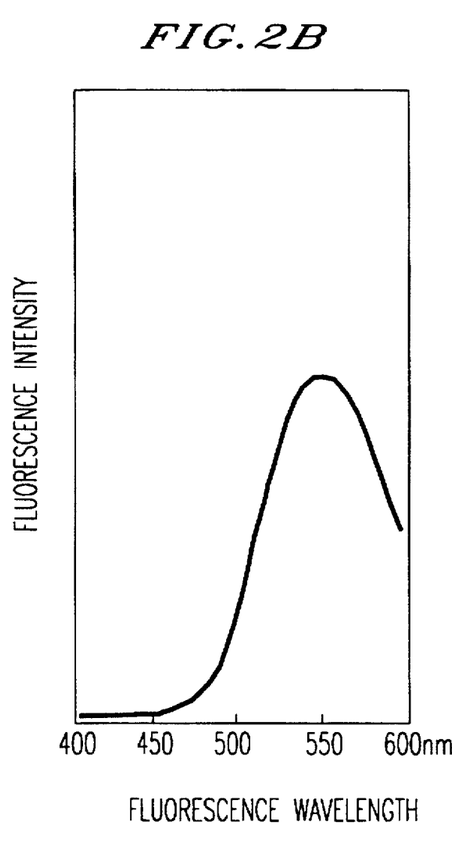
FIG. 2B shows an emission spectrum thereof for the excitation light of 325 nm thereof.

FIG. 2A shows the excitation spectrum of dansyl-L-alanine which is an example of the reference fluorescent substance. FIG. 2B shows the emission spectrum thereof. As is clear from FIGS. 1A, 1B, 2A, and 2B, in the case where the objective fluorescent substance is 4-methylumbelliferone and the reference fluorescent substance is dansyl-L-alanine, the excitation wavelength is selected preferably in the range of from 320 to 390 nm; the first measurement wavelength for measuring the first fluorescent intensity preferably in the range of from 420 to 500 nm; and the second measurement wavelength for measuring the second fluorescent intensity in the range of from 500 to 650 nm; more preferably the excitation wavelength is selected in the range of from 340 to 380 nm; the first measurement wave length from 430 to 480; and the second measurement wavelength from 540 to 630 nm.

In the equation, $1/(y-c)=a/x+b$, for the conversion in the present invention, the parameters a, b, and c are derived by measuring the first fluorescence intensities and the second fluorescence intensities for three or more concentrations (x) of a sample of an objective fluorescent substance including the concentration of zero, dividing the first fluorescence intensity by the second fluorescence intensity to obtain the value of "y", and so forth. Specifically the procedure is as follows.

(1) Reference specimens at three concentrations:

When three known concentrations (including zero) of reference specimens are employed, fluorescence measurement is conducted with the three specimens containing the objective fluorescent substance at the concentrations x ($x=0$, $x=x_1$, or $x=x_2$) and a fixed concentration of the reference fluorescent substance. The values of y ($y_0$, $y_1$, and $y_2$) are calculated for each concentration. Then, the simultaneous equations: $1/(y_1-c)=a/x_1+b$, and $1/(y_2-c)=a/x_2+b$ are solved for a and b by letting $c=y_0$. Thus values of a, b, and c are derived.

(2) Reference specimens at four or more concentrations:

When four or more known concentrations (including zero) of reference specimens of an objective fluorescent substance are employed, fluorescence measurement is conducted with the objective fluorescent substance at the concentrations x ($x=0$, $x=x_1$, $x=x_2$, ... $x=x_n$) and a fixed concentration of the reference fluorescent substance. The ratios y ($Y_0$, $Y_1$, $Y_2$, ... $y_n$) are calculated for respective concentrations. Then, from the set of data of ($X_i$, $Y_i$) (where $c=y_0$, $Y_i=1/(y_{i-c})$, and $X_i=1/x_i$), a regression line, $Y=aX+b$, is derived by a least square method with weighting factors increasing with increase of $x_i$ to obtain the values of a and b. The weighting herein means a factor $w_i$ in calculation of the sum of square of errors ($\Sigma w_i(Y-Y_i)^2$:$i=1, 2, \ldots n$).

The calculation procedure is explained for the cases in which one of the reference specimens contains no objective fluorescent substance (concentration zero). This is particularly preferred for simplifying the calculation with accuracy, especially at a low concentration range of the objective fluorescent substance. However it is not always necessary to calculate the parameter a, b, and c that the concentration of an objective fluorescent substance in one of the reference specimens is zero. It is required to improve the accuracy of conversion in a low concentration of the objective fluorescent substance that the concentration of an objective fluorescent substance in one of the reference specimens is nearly zero. However, the concentration of zero is not always necessary, provided that one of the reference specimen contains the objective substance at a low concentration.

When three concentrations of reference specimens are employed without a specimen of concentration zero, fluorescence measurement is conducted with the three specimens containing the objective fluorescent substance at the known concentrations x ($x=x_0$, $x=x_1$, or $x=x_2$) and a fixed concentration of the reference fluorescent substance. The ratios y ($y_0$, $y_1$, and $y_2$) are calculated for respective concentrations. Then, the simultaneous equations: $1/(y_0-c)=a/x_0+b$, $1/(y_1-c)=a/x_1+b$, and $1/(y_2-c)=a/x_2+b$ are solved to obtain a, b, and c.

When four or more known concentrations of reference specimens of the objective fluorescent substance are employed, the parameters a, b, and c can be obtained, regardless of the presence of specimens of concentration zero, by non-linear least square method. Fluorescence measurement is conducted with the specimens containing the objective fluorescent substance at the different concentrations x ($x=x_0$, $x=x_1$, $x=x_2$, ... $x=x_n$) and a fixed concentration of the reference fluorescent substance. The ratios y ($y_0$, $y_1$, $y_2$, ... $y_n$) are calculated for respective concentrations. Then, a, b, and c are calculated by applying non-linear least square method to the equation: $1/(y-c)=a/x+b$. In this calculation, non-linear least square method should be applied, since the equation is not linear to the parameter c. This method gives more precise values of the parameters a, b, and c. However, the calculation is complicated, and in some cases, the obtained values may diverge in the calculation. Therefore, care should be taken in application of this method.

The concentrations of the reference specimens are selected to include three or more concentration levels, preferably to include the concentration zero and the highest concentration in the measurement range of the objective fluorescent substance. However, the relation curve given by the calculation equation, $1/(y-c)=a/x+b$, of the present invention is approximate sufficiently to real fluorescence intensity, so that the highest concentration of the reference specimen may be about half of the possible highest concentration of the objective fluorescent substance. The highest concentration herein means the possible concentration of the objective fluorescent substance in the unknown specimens subjected practically to the measurement.

The method of the present invention can be conducted automatically by a fluorescence detector, which is composed with an excitation light-projecting system, a first light measurement system, a second light measurement system, and an electric signal-processing circuit: the excitation light-projecting system projects excitation light to a specimen containing an objective fluorescent substance, the first light measurement system receives selectively the first wavelength component from the fluorescence emitted from the specimen and converts it into an electric signal, the second light measurement system receives selectively the second wavelength component from the fluorescence emitted from the specimen and converts it into an electric signal, the electric signal-processing circuit processes the electric signals received from the light-receiving system.

The excitation light-projecting system of the fluorescence detector can be constituted from suitable combination of a light source, a filter, a mirror, a condenser lens, etc. The light-receiving system of the fluorescence detector is constituted of a first light-receiving system and a second light-receiving system, each light-receiving system being constituted of a mirror, a condenser lens, a filter, a light-sensor such as a photodiode and a photomultiplier, an amplifier, etc. The electric signal-processing circuit may be formed, for example, by combining suitably a microcomputer and an analog processing circuit.

More specifically, the optical system constituted of the light-projecting system and the light-receiving system has preferably a configuration of a top-top type in which the fluorescence emitted by the specimen is detected in the direction reverse to the excitation light projection direction to conduct fluorescence measurement efficiently and continuously. However, the fluorescence may be detected from the direction perpendicular to the excitation light projection direction. In the configuration of the top-top type, for example, a dichroic mirror is placed in the optical path of a light-projection system to project the light downward, and another dichroic mirror is placed in the optical path of a light-receiving system to separate the first fluorescence wavelength component and the second fluorescence wavelength component of the received light, and the respective fluorescence components are detected by separate light-receiving sensors. In this example, a half mirror may be used in place of the dichroic mirror.

The processing by an electric signal processing circuit includes calculation of division of the electric signal from the first light-receiving system by the electric signal for the second light-receiving system. The results may be converted subsequently into digital signals by an A/D converter. If the respective electric signals are converted preliminarily into digital signals by A/D converters, the signal can be processed by digital signal processing circuit such as a digital computer.

As described above, the calculation processing for the present invention can be conducted also by a usual microcomputer, etc. as well as a digital processing circuit such as a digital computer.

The decrease of the apparent fluorescence intensity caused by self-absorption of the excitation light, which is remarkable, for example, in high concentration of the objective fluorescent substance, can be corrected by using the ratio of the fluorescence intensity of an objective fluorescent substance to that of a reference fluorescent substance in the prior-art method of conversion. However, in this method, at a high concentrations of the objective fluorescent substance, the linearity of the calibration curve for the determination is impaired owing to unavoidable mixing of fluorescence from the objective fluorescent substance and that from the reference fluorescent substance. Therefore, remarkable improvement in measurement accuracy cannot be achieved by the prior-art method. In contrast, the present invention makes practicable the measurement of a fluorescent substance in a broader concentration range with higher accuracy. Moreover, in the present invention, the parameters required for the conversion calculation can be derived simply by use of three or more standard samples to fit the conversion calculation curve to practical fluorescence intensity. In particular, it is understood from FIGS. 5, 6, 7, and 8 that the present invention makes practicable the measurement at higher concentrations with high accuracy.

As described above, the present invention broadens the measurement range and raises the precision of the measurement, and is suitable for measurement of an objective fluorescent substance such as a fluorescent substance formed by enzyme action in enzyme-label immunoassay or enzyme-label DNA hybridization.

The present invention is described below in more detail by reference to examples without limiting the invention in any way.

Figure 3:
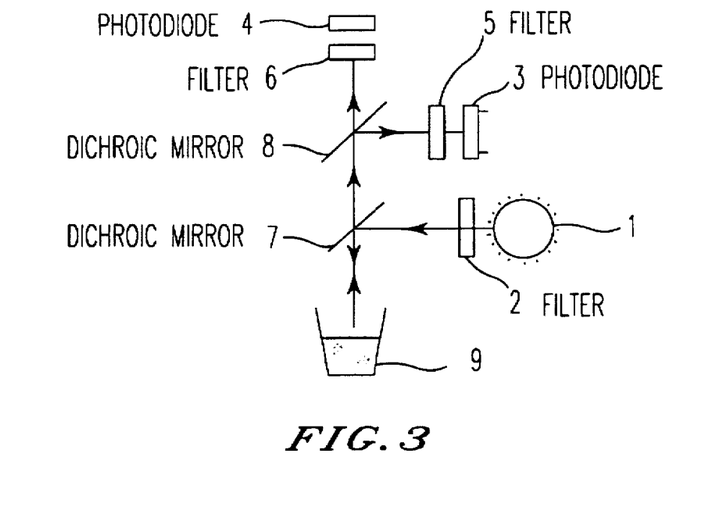
FIG. 3 illustrates the fluorescence detector employed in Examples.

FIG. 3 illustrate schematically the fluorescence detector employed in the examples. This detector has a top-top optical system. In FIG. 3, the numeral 1 indicates a light source, a fluorescent lamp having the peak wavelength of 365 nm; the numeral 2, a filter having a transmission range of from 320 to 380 nm; the numerals 3 and 4, respectively a photodiode as the light-receiving element; the numeral 5, a filter having a transmission range of from 575 to 625 nm; the numeral 6, a filter having a transmission range of from 405 to 480 nm; the numeral 7, a dichroic mirror transmitting the light of wavelength of longer than 400 nm and reflecting the light of wavelength of shorter than 400 nm; and the numeral 8, a dichroic mirror transmitting the light of wavelength of from 420 to 530 nm and reflecting the light of wavelength of longer than 530 nm.

With this fluorescence detector, the excitation light emitted by the light source 1 is allowed to pass through the filter 2 to make the purity of the light higher, and is reflected by the dichroic mirror 7 to be projected downward to the specimen in a container 9. The excitation light excite the sample to emit fluorescence. The fluorescence emitted upward from the specimen is allowed to pass through the dichroic mirror 7, and is separated into a first light including the first fluorescence wavelength and a second light including the second fluorescence wavelength by the dichroic mirror 8. The first light travels upward, is allowed to pass through the filter 6 to have selected range of wavelength, and introduced to the light-receiving element 4, where the light is converted to electrical signals. On the other hand, the second light is allowed to pass through the filter 5 to have selected range of wavelength, and introduced to the light-receiving element 3, where the light is converted to electrical signals.

Figure 4A:
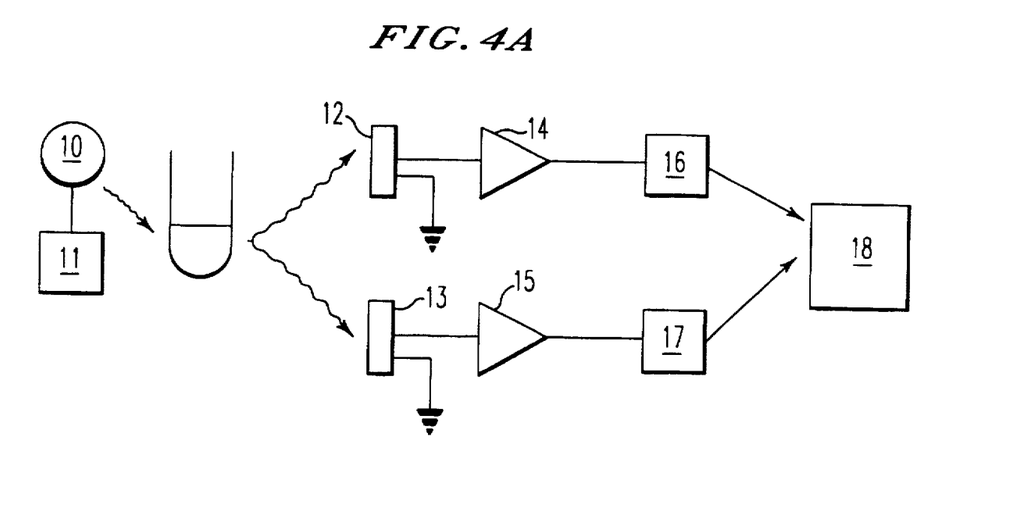
FIGS. 4A and 4B illustrate the flows of the signals in the fluorescence detector illustrated in FIG. 3.
Figure 4B:
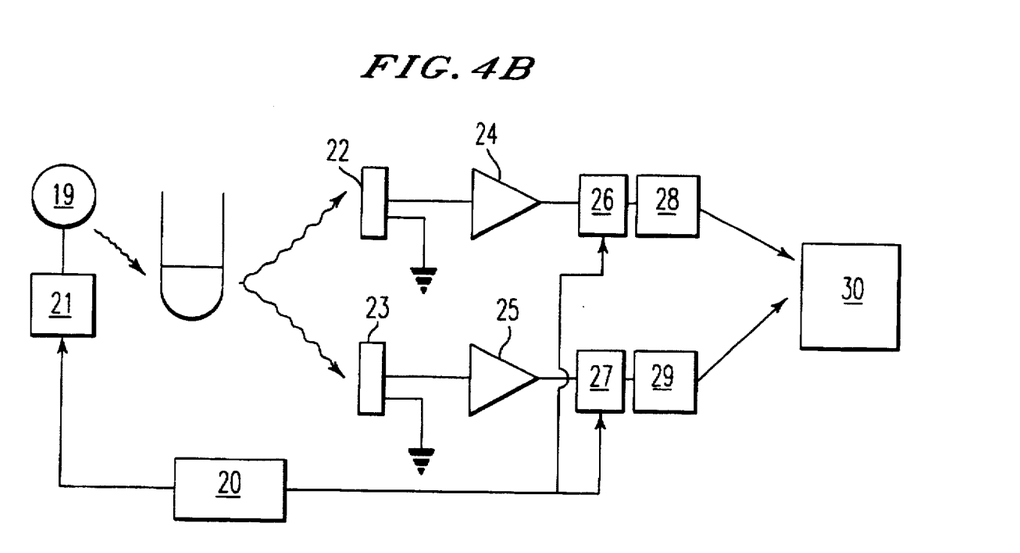

FIGS. 4A and 4B show flows of the signals in the fluorescence detectors in FIG. 3. FIG. 4A shows flows of the signals in the case where the light source is continuously turned on. FIG. 4B shows flows of the signals in the case where the light source is flickering. In Examples described later, a flickering light source is employed.

In FIG. 4A, the light source is kept turned on continuously by means of a DC power source 11 (or quasi-continuously by means of a high frequency power source), and the light is projected to the specimen. The fluorescence emitted by the specimen is separated into a first light including a first wavelength fluorescence and a second light including a second wavelength fluorescence by a dichroic mirror as described above. The first light and the second light are respectively converted into an electric signal by a light-receiving sensor 12 or 13 in correspondence with the fluorescence intensity. The electric signals are respectively amplified by an amplifier 14 or 15, and are converted into a digital signal by an A/D converter (analogue/digital converter) 16 or 17. The digital signals are processed for division calculation by a digital processing circuit (computer) 18.

In FIG. 4B, the light source is flickering at a frequency, for instance, of 165 Hz with a pulse power source 21 driven according to the signals from a clock pulse generating circuit 20 to irradiate the specimen. The fluorescence emitted by the specimen is separated into a first light including a first wavelength fluorescence and a second light including a second wavelength fluorescence by a dichroic mirror in the same manner as in FIG. 4A. The first light and the second light are respectively converted into an electric signal by a light-receiving sensor 22 or 23 in correspondence with the fluorescence intensity. The electric signals are respectively amplified by an amplifier 24 or 25, detected synchronously with the signals generated by the aforementioned clock circuit 20 in a phase-sensitive detection circuit 26 or 27, and converted into a digital signal by an A/D converter (analogue/digital converter) 28 or 29. The digital signals are processed for division calculation by a digital processing circuit (computer) 30.

Example 1

0.2 Milliliter of solution containing 4-methylumbelliferone respectively at a concentration of 0 µM, 10 µM, 20 µM, 30 µM, 40 µM, 50 µM, or 60 µM, and dansyl-alanine at a concentration of 0.1 mg/mL was placed in each measurement cup. The solution was subjected to measurement with a detector having the constitution shown in FIG. 3. The excitation wavelength and the fluorescence wavelength were as mentioned before. The results are shown in Table 1.

TABLE 1

| Concentration of 4-methylumbelliferone (µM) | Fluorescence intensity ratio |
|---|---|
| 0.0 | −0.01 |
| 10.0 | 8.02 |
| 20.0 | 18.89 |
| 30.0 | 18.37 |
| 40.0 | 21.93 |
| 50.0 | 24.75 |
| 60.0 | 27.10 |

Figure 5:
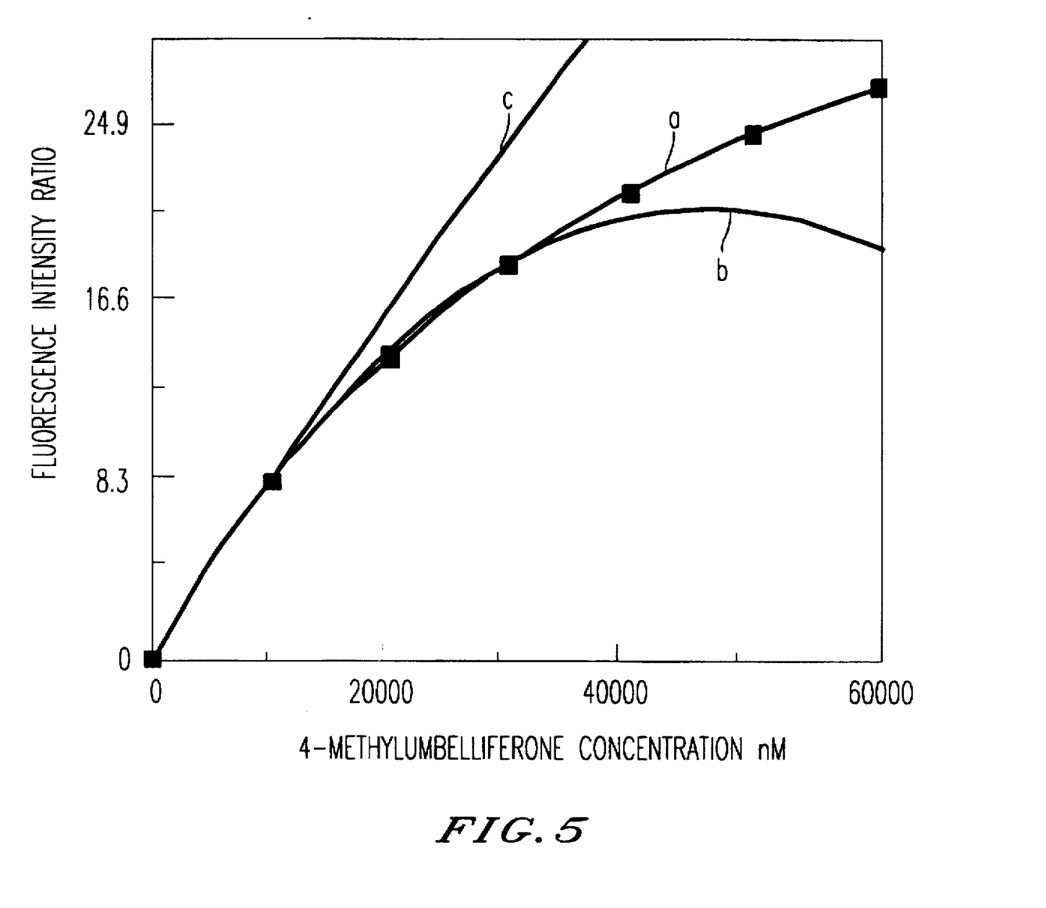
FIG. 5 shows the practically measured values (indicated by solid squares: ■) at seven concentrations of 4-methylumbelliferone including three concentrations of standard samples in Example 1, the calibration curve (a) according to the present invention, the calibration curve (b) according to the quadratic conversion equation, and the calibration curve (c) according to the linear conversion equation. The abscissa axis shows the concentration (nM) of 4-methylumbelliferone, and the ordinate axis shows the fluorescence intensity ratio. The calibration curve (a) is represented by the equation.

FIG. 5 shows the calibration curve (a) obtained according to the conversion equation of the present invention by using the parameters of a, b, and c derived from the data at the 4-methylumbelliferone concentrations of 0 µM, 10 µM, and 30 µM; a calibration curve (b) obtained according to a conventional conversion equation expressed by a quadratic equation $y=px^2+qx+r$, whose parameters p, q and r were obtained from the measured data of 0µM, 10 µM and 30 µM 4-methyl umbelliferone; a calibration curve (c) obtained according to a conventional conversion equation expressed by a liner equation $y=sx+t$, whose parameters s and t were obtained from the measured data of 0 µM and 10 µM 4-methyl unbelliferone; and the experimental data ( shown by solid squares) which are the ratios of the first fluorescence intensity and the second fluorescence intensity at the concentrations of 0 µM, 10 µM, 20 µM, 30 µM, 40 µM, 50 µM and 60 µM. of 4 methylumbelliferone.

The calibration curve obtained according to the conversion equation according to the present invention fits well the measured value even outside the concentration range of the standard samples, whereas the calibration curve obtained by regression to the conventional quadratic equation deviates remarkably from the measured data outside the concentration range of the standard samples.

Figure 6:
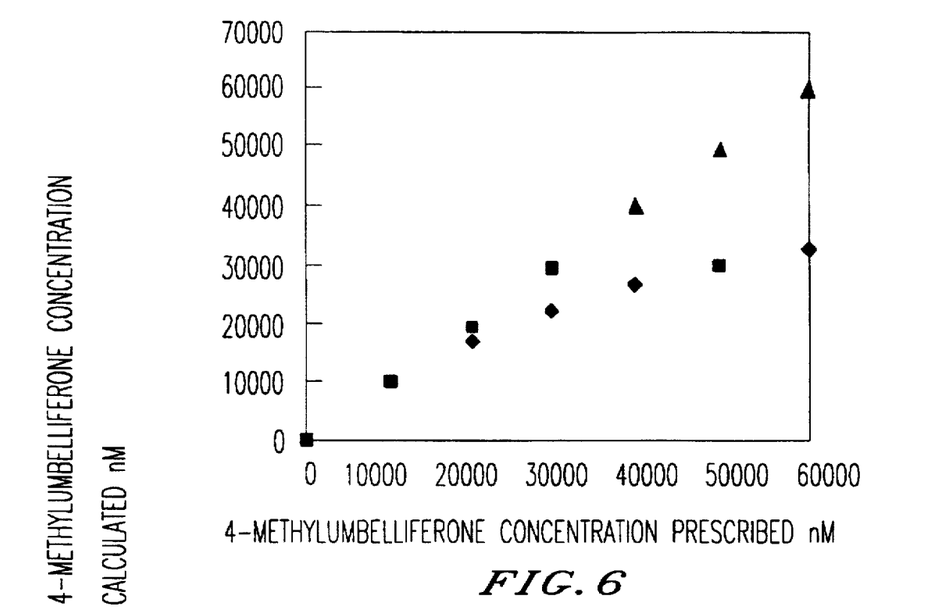
FIG. 6 shows the plots of the concentrations of 4-methylumbelliferone calculated from the measured data for the corresponding prescribed concentration thereof with the abscissa for the prescribed concentration and the ordinate for the calculated concentration.

FIG. 6 shows the relation between the prescribed concentration of 4-methylumbelliferone (real concentration), and the calculated concentration thereof obtained from the calibration curves shown in FIG. 5. In FIG. 6, the solid rhombus symbols show the results of linear conversion, the solid square symbols show the results of conversion by the quadratic equation, and the solid triangle symbols show the results of conversion according to the present invention. In FIG. 6, at the prescribed concentrations of 4-methylumbelliferone of 0 and 10.000 nM(10 µM), the triangle symbols, rhombus symbols, and the square symbols come to be superposed each other, and at the prescribed concentrations of 20.000 nM(20 µM) and 30,000 nM(30 µM), the triangle symbols and the square symbols come to be superposed each other. As shown in FIG. 6, in the conversion calculation by the quadratic equation or the linear equation, the mixing of the fluorescence of 4-methylumbelliferone with that of the reference fluorescent substance cannot be corrected, thereby precise correction or accurate conversion being impossible at higher concentrations, and the inherent linear relation cannot be obtained between the real concentration and the calculated concentration. By contrast, the linear relation for these values can be achieved according to the present invention. In the concentration range of from 0 to 10.000 nM (10 µM), the results of the conversion calculation according to the present invention and results according to the quadratic equation coincide well. However, in the concentration range above 30.000 nM (30 µM), the conversion calculation by the quadratic equation does not give the concentration of 4-methylumbelliferone, and in the concentration range above 20.000 (20 µM), the calculation by the linear equation gives concentration much different from the real value.

Figure 7:
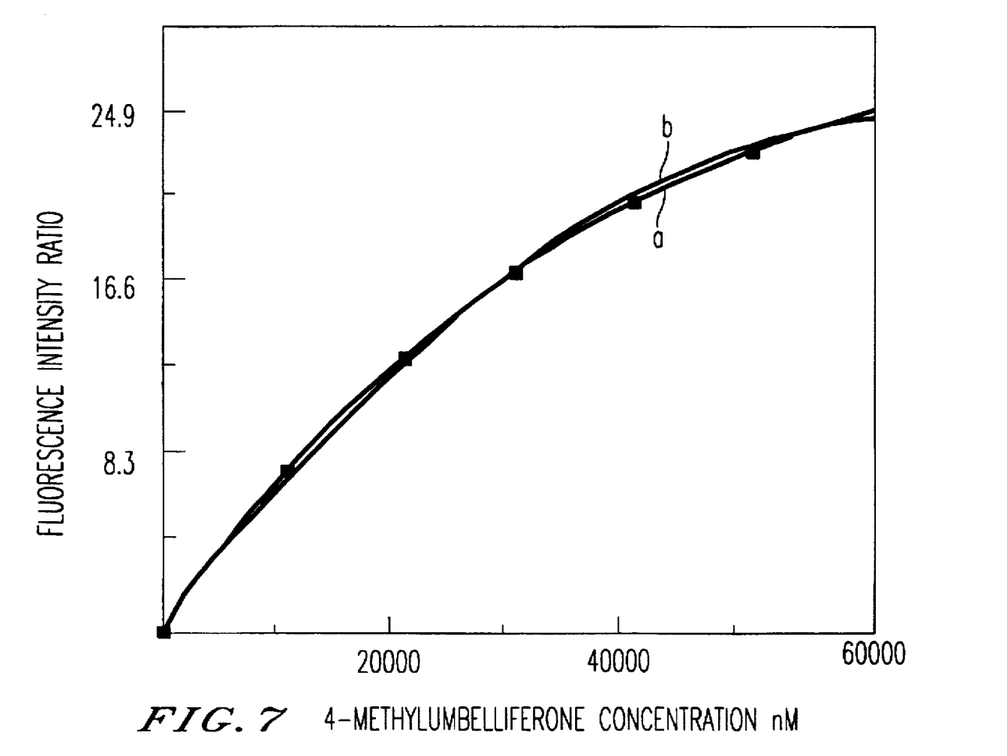
FIG. 7 shows the calibration curve (a) of the present invention, the calibration curve (b) according to the quadratic equation, and practically measured fluorescence intensity ratios (indicated by solid square symbols) for the prescribed concentrations in the 4-methylumbelliferone concentration measurement in Example 1 when the conversion equations were derived from seven reference specimens. The abscissa axis shows the concentration (nM) of 4-methylumbelliferone, and the ordinate axis shows the fluorescence intensity ratio. The calibration curve (a) is represented by the equation.

FIG. 7 shows the calibration curves (a) and (b), and practically measured fluorescence intensity ratios (indicated by solid square symbols) for the prescribed concentrations. The calibration curve (a) was obtained from the conversion equation of the present invention based on the parameters a, b, and c derived from measured data at the 4-methylumbelliferone concentrations of 0 µM, 10 µM, 20 µM, 30 µM, 40 µM, 50 µM, and 60 µM. The calibration curve (b) was obtained from regression to the conventionally used quadratic equation at the same concentrations as above.

In FIG. 7, in deriving the parameters a, b, and c for the calibration curve (a), weighting factors are multiplied in proportion to the concentration. The weighting factors were 1, 2, 3, 4, 5, and 6 respectively corresponding to the concentrations of 10 µM, 20 µM, 30 µM, 40 µM, 50 µM, and 60 µM.

The calibration curve obtained from the conversion equation of the present invention fits well the real values. However, the calibration curve obtained by regression to the quadratic equation deviates from the real values at concentrations of around zero, around 10 to 20 µM, around 40 to 50 µM, and around 60 µM.

Example 2

The enzyme activity of alkaline phosphatase was determined by measuring the change (increase) with time of 4-methylumbelliferone, the enzymatic reaction product.

Into a measurement cup, were added 10 µL of a solution containing alkaline phosphatase in a concentration of 50 nM/s (having an activity of forming 50 nM of 4-methylumbelliferone per second, when 10 µL of the solution is mixed with 200 µL of the 1 mM of 4-methylumbelliferyl phosphate solution) or 500 nM/s (having an activity of forming 500 nM of 4-methylumbelliferone per second, when 10 µL of the solution is mixed with 200 µL of the 1 mM of 4-methylumbelliferyl phosphate solution), and 0.2 mL of a solution containing 0.1 mg/mL of dansyl-alanine as the reference fluorescent substance and 1 mM of 4-methylumbelliferyl phosphate as the substrate with agitation. After addition of the 4-methylumbelliferyl phosphate, the increase with time of the concentration of 4-methylumbelliferone formed by enzymatic action of the alkaline phosphatase was measured by employing the excitation light and at the measurement wavelength for the fluorescent as mentioned above.

Figure 8:
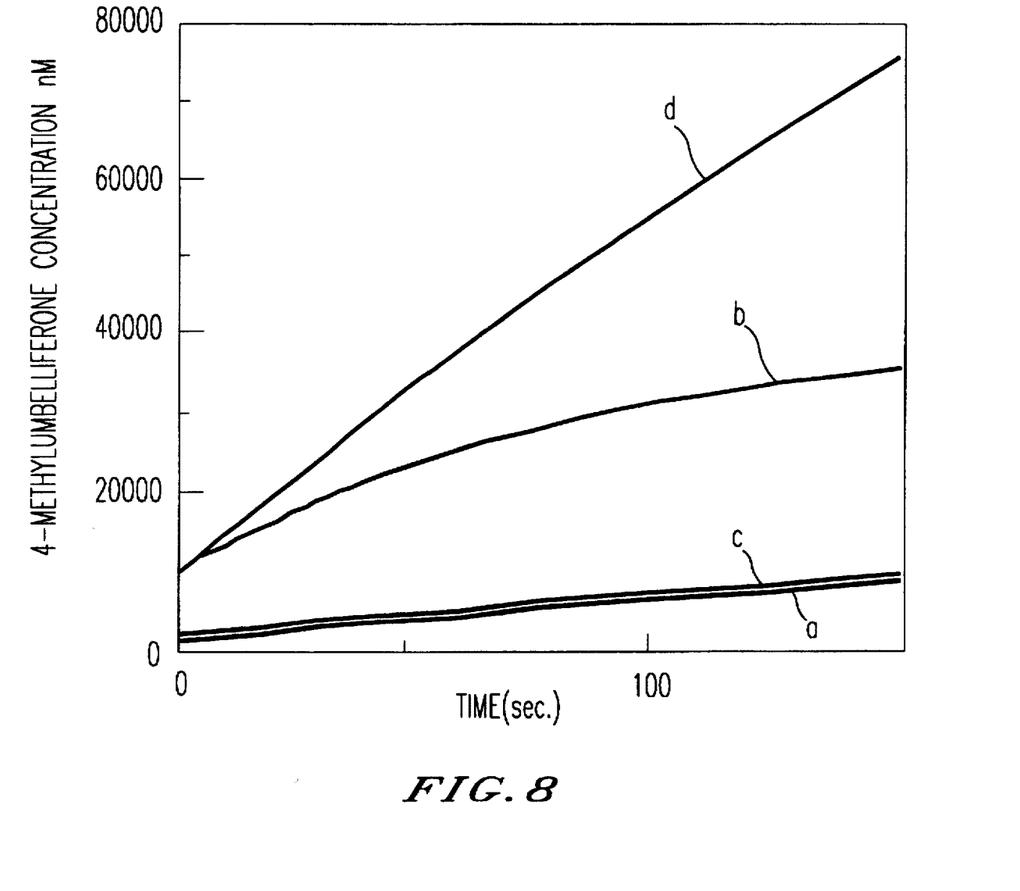
FIG. 8 illustrates the results of Example 2, showing the change with time of the concentration of 4-methylumbelliferone formed by action of the alkaline phosphatase with the data (a) and (b) obtained by conversion calculation by the linear equation and with the data (c) and (d) obtained by conversion calculation according to the present invention. The ordinate axis shows the concentration (nM) of 4-methylumbelliferone, and the abscissa shows the time (seconds).

FIG. 8 shows the increase with time of the 4-methylumbelliferone concentration by action of the alkaline phosphatase. In FIG. 8, the symbol (a) indicates the results obtained according to the linear conversion equation and the symbol (c) indicates the results obtained according to the conversion equation of the present invention, for the alkaline phosphatase concentration of 50 nM/s. The symbol (b) indicates the results obtained according to the linear conversion equation and the symbol (d) indicates the results obtained according to the conversion equation of the present invention, for the alkaline phosphatase concentration of 500 nM/s. The data (y) before the conversion calculation were the ratios of the first fluorescence intensity to the second fluorescence intensity, which are the quotients derived by dividing the measured fluorescence intensity of 4-methylumbelliferone by that of dansyl-alanine (namely, relative fluorescence intensities), the linear conversion and the conversion curve according to the present invention are respectively the conversion curve defined in FIG. 5 Thus the conversion equation for the linear conversion is $y=sx+t$ in which $s=0.805\times10^{-3}nM^{-1}$ and $t=-0.01$, while the conversion equation according to the present invention is $1/(y-c) =a/x+b$ in which $a=10.48\times10^3 nM$, $b=0.193$, and $c=-0.01$.

Example 3

At different concentrations of alkaline phosphatase, the change with lapse of time of the concentration of 4-methylumbelliferone formed by action of the alkaline phosphatase was measured. The rate of the change herein is called "Rate" (rate of increase of 4-methylumbelliferone per second (nM/s)).

A solution of 1000 nM/s alkaline phosphatase was diluted to a series of relative concentrations of 0.1, 0.2, 0.3, 0.4, 0.5, 0.6, 0.7, 0.8, 0.9 and 1.0 (undiluted). Fractions of 10 µL of the diluted solutions was respectively added to 0.2 mL portions of a solution containing 0.1 mg/mL of dansyl-alanine as the reference fluorescent substance and 1 mM of 4-methylumbelliferyl phosphate as the substrate. After the addition of 4-methylumbelliferyl phosphate, the increase with time of 4-methylumbelliferone formed by enzymatic action of the alkaline phosphatase was measured by employing the aforementioned excitation wavelength and the fluorescence wavelengths.

Figure 9:
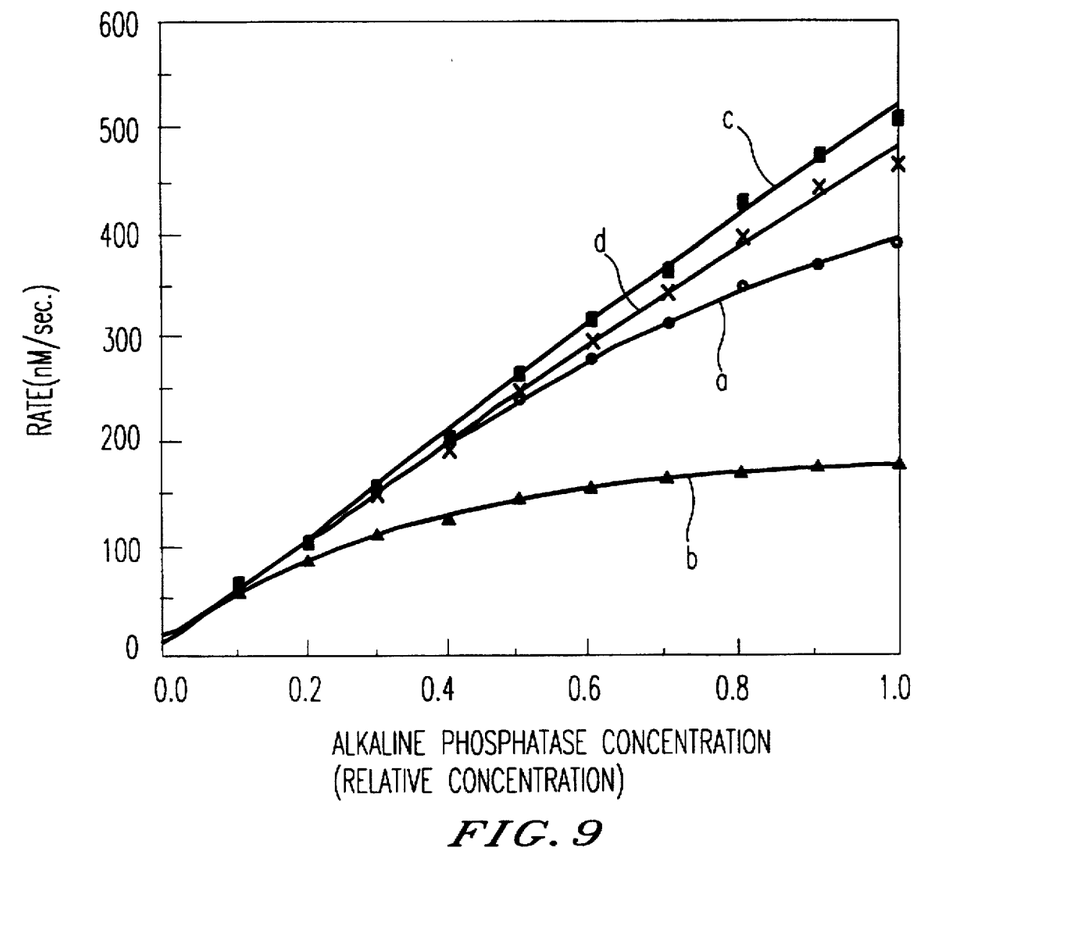
FIG. 9 illustrates the results of Example 3, showing the change with time (Rate: nM/s) of 4-methylumbelliferone concentration as a function of the alkaline phosphatase concentration with the data (a) and (b) obtained by conversion calculation by the linear equation and with the data (c) and (d) obtained by conversion calculation according to the present invention. The ordinate axis shows the change with time (Rate: nM/s) of 4-methylumbelliferone, and the abscissa shows the alkaline phosphatase concentration (relative concentration)

The results are shown in FIG. 9. The Rate (the change rate (µM/s)) of 4-methylumbelliferone concentration was derived from the change with time of the concentration calculated by the linear conversion equation, or the conversion equation of the present invention. In FIG. 9, the curve (a) shows the Rate derived from the change of the concentration calculated by the linear equation 10 seconds and 20 seconds after the addition of 4-methylumbelliferyl phosphate namely the change during 10 seconds, and the curve (c) shows the Rate under the same conditions but calculated by the conversion equation of the present invention. The curve (b) shows the Rate derived from the change of the concentration calculated by the linear equation from 10 seconds to 150 seconds after the addition of 4-methylumbelliferyl phosphate namely the change during 140 seconds; the curve (d) shows the Rate under the same conditions but calculated by the conversion equation of the present invention.

The data before the conversion calculation were the ratios (or quotients) derived by dividing the measured fluorescence intensity of 4-methylumbelliferone by that of dansyl-alanine (namely, relative fluorescence intensities), the linear conversion and the conversion curve according to the present invention are respectively the conversion curve defined in FIG. 5. Thus the conversion equation for the linear conversion is $y=sx+t$ in which $s=0.805 \times 10^{-3}$ $nM^{-1}$ and $t=-0.01$, while the conversion equation according to the present invention is $1/(y-c)=a/x+b$ in which $a=10.48 \times 10^3$ nM, $b=0.193$, and $c=-0.01$.

In FIG. 9, the curves (a) and (b) showing the Rates which were derived from the change with time of the concentration calculated from the fluorescence intensities deviates from the inherent linear relation owing to leakage of the fluorescence of the increasing 4-methylumbelliferone to the second fluorescence intensity (which is derived for the fluorescence of the reference fluorescent substance). However, the curves (c) and (d) are linear which were derived by conversion calculation with the measured data according to the present invention. The larger deviation of the curve (b) from the linearity than the curve (a) is presumably due to the measurement conducted to higher concentrations. The lower values of the curve (d) than the curve (c) is presumably due to the consumption of 4-methylumbelliferyl phosphate as the substrate with the progress of the enzymatic reaction. Incidentally, in this Example, at the initial alkaline phosphatase concentration of 500 nM/s, 7.5% of the substrate had been consumed during 150 seconds after the start of the enzyme reaction.

What is claimed is:

1. A method for determining the concentration of a fluorescent substance, comprising adding a known amount of a reference fluorescent substance to a specimen containing an objective fluorescent substance to be determined; irradiating the specimen with excitation light capable of exciting both the objective fluorescent substance and the reference fluorescent substance; measuring a first fluorescence intensity at a first wavelength where fluorescence is emitted mainly by the objective fluorescent substance; measuring a second fluorescence intensity at a second wavelength where fluorescence is emitted mainly by the reference fluorescent substance; and calculating the concentration of the objective fluorescent substance from the equation:

$$1/(y-c)=a/x+b$$

where x is the concentration of the objective fluorescent substance, y is a ratio of the first fluorescence intensity to the second fluorescence intensity, and a, b and c are constants determined by measuring fluorescence intensities of reference specimens containing at least three different concentrations of the objective fluorescent substance.

2. A method for assaying activity of an enzyme by measuring change with time of concentration of an objective fluorescent substance by action of the enzyme, comprising adding a known concentration of a reference fluorescent substance to a specimen containing an objective fluorescent substance to be determined; irradiating the specimen with excitation light capable of exciting both the objective fluorescent substance and the reference fluorescent substance; measuring a first fluorescence intensity at a first wavelength where fluorescence is emitted mainly by the objective fluorescent substance; measuring a second fluorescence intensity at a second wavelength where fluorescence is emitted mainly by the reference fluorescent substance; calculating the concentration of the objective fluorescent substance from the equation:

$$1/(y-c)=a/x+b$$

where x is the concentration of the objective fluorescent substance, y is a ratio of the first fluorescence intensity to the second fluorescence intensity, and a, b and c are constants determined by measuring fluorescence intensities of reference specimens containing at least three different concentrations of the objective fluorescent substance; and deriving the activity of the enzyme or the concentration of the enzyme from the change with time of the value of x.

3. The method according to claim 1 or claim 2, wherein the fluorescence intensities of reference specimens contain three different known concentrations ($x=x_1$, $x=x_2$, and $x_3$) of the objective fluorescent substance and a fixed concentration of a reference fluorescent substance are measured to obtain the first fluorescence intensities and the second fluorescence intensities at the respective concentrations, the ratios of the first fluorescent intensity to the second fluorescence intensity at the respective concentrations ($y_1$, $y_2$, and $y_3$) are derived, and therefrom a, b, and c in the conversion formula, $1/(y-c)=a/x+b$, are determined, and thereby calculating the value of x.

4. The method according to claim 1 or claim 2, wherein the fluorescence intensities of reference specimens contain three different known concentrations including concentration of zero ($x=0$, $x=x_1$ and $x=x_2$) of the objective fluorescent substance and a find concentration of a reference fluorescent substance are measured to obtain the first fluorescence intensities and the second fluorescence intensities at the respective concentrations, the ratios of the first fluorescent intensity to the second fluorescence intensity at the respective concentrations ($y_0$, $y_1$, and $y_2$) are derived, and therefrom, a and b in the conversion formula are determined, by letting $c=y_0$ and solving the simultaneous equations: $1/(y_1-c)=a/x_1+b$, and $1/(y_2-c)=a/x+b$, and thereby calculating the value of x according to the equation: $1/(y-c)=a/x+b$.

5. The method according to claim 1 or claim 2, wherein the fluorescence intensities of reference specimens containing four or more different known concentrations including concentration of zero ($x=0$, $x=x_1$, $x=x_2$, ..., $x_n$, where n is an integer of 3 or more) of the objective fluorescent substance and a fixed concentration of a reference fluorescent substance are measured to obtain the first fluorescence intensities and the second fluorescence intensities at the respective concentrations, the ratios of the first fluorescent intensity to the second fluorescence intensity at the respective concentrations ($y_0$, $y_1$, $y_2$, ..., $y_n$) are derived, a and b in the conversion formula are determined by least square regression to $Y=aX+b$ with weighting of data sets of ($X_i$, $Y_i$) where $c=y_0$, $Y_i=1/(y_i-c)$, and $X_i=1/x_i$ with factors which increase with increase of $x_i$, and calculating the value of x according to the equation: $1/(y-c)=a/x+b$.

* * * * *